(12) United States Patent
Xie et al.

(10) Patent No.: US 8,669,392 B2
(45) Date of Patent: Mar. 11, 2014

(54) PROCESS FOR PREPARING 2,3-DI-NON-STRAIGHT-ALKYL-2-CYANOSUCCINIC ACID DIESTERS

(75) Inventors: Lunjia Xie, Beijing (CN); Yu Tian, Beijing (CN); Zaixing Feng, Beijing (CN); Siyuan Zhao, Beijing (CN); Yu Kang, Beijing (CN); Zhufang Sun, Beijing (CN)

(73) Assignees: China Petroleum & Chemical Corporation, Beijing (CN); Beijing Research Institute of Chemical Industry, China Petroleum & Chemical Corporation, Beijing (CN)

( * ) Notice: Subject to any disclaimer, the term of this patent is extended or adjusted under 35 U.S.C. 154(b) by 89 days.

(21) Appl. No.: 13/202,282

(22) PCT Filed: Feb. 12, 2010

(86) PCT No.: PCT/CN2010/000202
§ 371 (c)(1),
(2), (4) Date: Oct. 28, 2011

(87) PCT Pub. No.: WO2010/094211
PCT Pub. Date: Aug. 26, 2010

(65) Prior Publication Data
US 2012/0046490 A1    Feb. 23, 2012

(30) Foreign Application Priority Data
Feb. 19, 2009   (CN) .......................... 2009 1 0077779

(51) Int. Cl.
*C07C 253/30*   (2006.01)
*C07C 67/32*    (2006.01)
*C07C 51/38*    (2006.01)

(52) U.S. Cl.
USPC ........................... 558/378; 560/190; 562/590

(58) Field of Classification Search
None
See application file for complete search history.

(56) References Cited

U.S. PATENT DOCUMENTS

| | | |
|---|---|---|
| 4,428,887 A | 1/1984 | Tou et al. |
| 4,442,298 A | 4/1984 | Tou et al. |
| 6,818,583 B1 | 11/2004 | Morini et al. |

FOREIGN PATENT DOCUMENTS

| | | |
|---|---|---|
| CN | 1313869 A | 9/2001 |
| WO | WO 00/63261 A1 | 10/2000 |

OTHER PUBLICATIONS

C.S. Marvel et al., "The Synthesis and Polymerization of Some 2-Methyl-3-alkyl-1,3-butadienes", *Journal of the American Chemical Society*, vol. 74, No. 6, Mar. 20, 1952, pp. 1506-1509.
Extended European Search Report for International Patent Application No. 10743392.2 dated Oct. 16, 2012.
International Search Report for PCT/CN2010/000202 mailed May 20, 2010.
Santoro et al., "enantioselective organocatalytic substitution of a-cyanoacetates on imidoyl chlorides—synthesis of optically active ketimines", *Chem.Commun.*, 2007, pp. 5155-5157.

*Primary Examiner* — Alicia L Otton
(74) *Attorney, Agent, or Firm* — Finnegan, Henderson, Farabow, Garrett & Dunner, LLP (57) ABSTRACT

A process for preparing 2,3-di(non-linear-alkyl)-2-cyanosuccinate compounds, especially 2,3-diisopropyl-2-cyanosuccinate compounds, and processes for preparing 2,3-di(non-linear-alkyl)succinic acids and esters thereof by using the 2,3-di-non-linear propyl-2-cyanosuccinate compounds as intermediates are disclosed.

16 Claims, 3 Drawing Sheets

Fig. 1

Process flow chart of the synthesis of diethyl 2,3-diisopropyl-2-cyanosuccinate

Fig. 2

Process flow chart of the synthesis of 2,3-diisopropylsuccinic acid

Fig. 3

Process flow chart of the synthesis of diethyl 2,3-diisopropylsuccinate

PROCESS FOR PREPARING 2,3-DI-NON-STRAIGHT-ALKYL-2-CYANOSUCCINIC ACID DIESTERS

CROSS REFERENCE OF RELATED APPLICATION

The present application is the U.S. National Stage of International Application No. PCT/CN2010/000202, which claims the priority of Chinese Application No. CN200910077779.6 filed on Feb. 19, 2009, which is incorporated herein by reference in its entirety and for all purposes.

FIELD OF THE INVENTION

The present invention relates to a process for the synthesis of a 2,3-di(non-linear-alkyl)-2-cyano-succinate compound and use of the compound as an intermediate in the preparation of a 2,3-diisoalkylsuccinic acid and esters thereof.

BACKGROUND ART

Seeking ideal electron donor compounds has been being a hot point of the studies on novel polypropylene catalysts. Chinese patent application CN1313869A discloses the use of 2,3-dihydrocarbylsuccinate compounds as a catalyst component in the preparation of a solid catalyst for olefin polymerization, among these compounds 2,3-diisopropylsuccinates being especially preferred internal electron donor compounds. As internal electron donor of Ziegler-Natta catalysts, this class of succinates improves the ability of the catalysts controlling molecular weight distributions, isotacticities and oligomer content of olefin polymers. Current Petrochemical Industry, 2003, Vol. 11(10), 4-11 reports that an impact copolymer, which is produced by using a propylene polymerization catalyst containing such a 2,3-dihydrocarbylsuccinate as electron donor, has balanced rigidity and impact property.

CN1313869A further discloses a process for the synthesis of the 2,3-dihydrocarbylsuccinates, comprising esterification, alkylation, reduction, oxidative coupling, $S_N2$ coupling, and combinations thereof. For example, CN1313869A discloses in Example 18 the preparation of diethyl 2,3-dipropylsuccinate through the oxidative coupling of ethyl pentanoate under the action of diisopropylamido lithium and $TiCl_4$, and in Example 22 the preparation of diethyl 2,3-dicyclohexylsuccinate through the esterification of 2,3-diphenylsuccinic acid and the reduction of phenyl to cyclohexyl.

However, for the preparation of 2,3-non-linear-alkyl-succinate compounds, no ideal process is disclosed in the prior art. The non-linear-alkylation, especially isoalkylation or sec-alkylation, of a diester of succinic acid on 2- and 3-positions are generally difficult due to large steric hindrance, and the yield is relatively low. The oxidative coupling method mentioned in CN1313869A requires the use of diisopropylamido lithium (LDA) prepared from hazardous material, n-butyl lithium, and the reaction is carried out at a temperature of −70° C.

As for the synthesis of a 2,3-di(non-linear-alkyl)-2-cyano-succinate compound, although literatures, J. Am. Chem. Soc. 1952, 74, 1056-1059 and Bull. Soc. Chim. Fr. 1975, (9-10, Pt. 2), 2189-2194, report referable methods, for example, one wherein a 2,3-dialkyl-2-cyanosuccinate compound may be prepared by alkylating a 3-alkyl-2-cyanosuccinate compound with a bromoalkane in three times amount or an expensive iodoalkane as alkylating agent, the product 2,3-dialkyl-2-cyanosuccinate compound has a boiling point close to the boiling point of the reactant 3-alkyl-2-cyanosuccinate compound so that isolation process such as rectification are difficult to be carried out, and for a reactant having large steric hindrance, such as 3-non-linear-alkyl-2-cyanosuccinate compound, the non-linear-alkylation on 2-position is more difficult.

Thus, there is still need for a novel process for the synthesis of a 2,3-di(non-linear-alkyl)succinate compound, which process may provide the 2,3-di(non-linear-alkyl)succinate compound under mild conditions at a relatively high yield. Furthermore, there is also need for a process that can prepare at industrial scale 2,3-di(non-linear-alkyl)-2-cyano-succinate compound as an intermediate of the 2,3-di(non-linear-alkyl)succinate compounds.

SUMMARY OF THE INVENTION

The inventors have made diligently studies. As a result, the inventors have found that a 2-non-linear-alkyl-2-cyanoacetate may react with a metal alkoxide to form a metal salt of enol (or its tautomer), and then said metal salt of enol may react with a 2-bromo-2-non-linear-alkylacetate to form a 2,3-di(non-linear-alkyl)-2-cyanosuccinate compound, which may be further converted to a 2,3-di(non-linear-alkyl)succinic acid and a 2,3-di(non-linear-alkyl)succinate. The process according to the present invention is especially suitable for the preparation of a 2,3-diisoalkyl-2-cyanosuccinate compound, a 2,3-diisoalkylsuccinic acid and a 2,3-diisoalkylsuccinate.

Thus, an object of the present invention is to provide a process for the preparation of a 2,3-di(non-linear-alkyl)-2-cyanosuccinate compound.

Another object of the present invention is to provide a process for the preparation of a 2,3-di(non-linear-alkyl)succinic acid.

A still another object of the present invention is to provide a process for the preparation of a 2,3-di(non-linear-alkyl)succinate.

DESCRIPTION OF PREFERRED EMBODIMENTS

The present invention provides a novel process for the synthesis of a 2,3-di(non-linear-alkyl)succinate compound, which process avoids the use of diisopropylamido lithium (LDA) prepared from hazardous material, n-butyl lithium, as well as low temperature operation at −70° C., thereby rendering the commercial production of 2,3-diisoalkyl succinates as internal electron donor in a polypropylene catalyst easy.

In a first aspect, the present invention provides a process for the preparation of a 2,3-di(non-linear-alkyl)-2-cyanosuccinate compound of the formula (I):

(I)

wherein, $R^1$ and $R^2$ are independently selected from the group consisting of linear $C_1$ to $C_{20}$ alkyl, branched $C_1$ to $C_{20}$ alkyl, $C_3$ to $C_{20}$ cycloalkyl, $C_4$ to $C_{20}$ alkylcycloalkyl, $C_4$ to $C_{20}$ cycloalkylalkyl, $C_6$ to $C_{20}$ aryl, $C_7$ to $C_{20}$ alkaryl and $C_7$ to $C_{20}$ aralkyl, preferably $C_1$ to $C_8$ alkyl, and more preferably methyl, ethyl, propyl, butyl and iso-butyl, and R is independently selected from the group consisting of $C_3$ to $C_6$ isoalkyl, $C_3$ to $C_6$ sec-alkyl and $C_3$ to $C_6$ cycloalkyl, and preferably isopropyl or iso-butyl, which process comprises the steps of:

(i) reacting a 2-non-linear-alkyl-2-cyanoacetate of the formula (II)

(II)

with a metal alkoxide in an alcohol solvent;

(ii) removing the alcohol solvent to obtain a concentrate;

(iii) dissolving the concentrate from (ii) in an aprotic solvent, and then reacting with a 2-bromo-2-non-linear-alkylacetate of the formula (III), to form a 2,3-di(non-linear-alkyl)-2-cyanosuccinate of the formula (I), (III)

wherein, in the formulae (II) and (III), R, $R^1$ and $R^2$ are as defined above for the formula (I).

In an embodiment, the metal alkoxide is selected from the group consisting of potassium methoxide, potassium ethoxide, potassium propoxide, potassium isopropoxide, potassium butoxide, potassium iso-butoxide, potassium tert-butoxide, sodium methoxide, sodium ethoxide, sodium propoxide, sodium isopropoxide, sodium butoxide, sodium iso-butoxide, sodium tert-butoxide and mixtures thereof. The metal alkoxide is preferably selected from the group consisting of potassium methoxide, potassium ethoxide, potassium tert-butoxide, sodium methoxide, sodium ethoxide, sodium tert-butoxide and mixtures thereof, and more preferably potassium ethoxide.

In an embodiment, a molar ratio of the compound of the formula (II) to the metal alkoxide is from 1:0.8 to 1:1.2, preferably from 1:1 to 1:1.2, and more preferably about 1:1.

In an embodiment, the alcohol solvent is selected from the group consisting of methanol, ethanol, propanol, isopropanol, butanol, iso-butanol, tert-butanol and mixtures thereof. The alcohol solvent is preferably selected from the group consisting of methanol, ethanol, tert-butanol and mixtures thereof, and more preferably ethanol.

In an embodiment, the amount of the alcohol solvent used ranges from 1 to 50 ml of alcohol per gram of the compound of the formula (II), preferably from 10 to 40 ml of alcohol per gram of the compound of the formula (II), and more preferably from 15 to 25 ml of alcohol per gram of the compound of the formula (II).

In an embodiment, the reaction temperature in step (i) is from −10° C. to 45° C., preferably from −5° C. to 40° C., and more preferably room temperature (about 25° C.). The reaction in step (i) can be performed conveniently under a normal pressure.

In an embodiment, the concentration temperature in step (ii) is one required by the atmospheric distillation of the alcohol solvent or the vacuum distillation of the alcohol solvent.

In an embodiment, the aprotic solvent is selected from the group consisting of tetrahydrofuran, dimethyl formamide, dimethyl sulfoxide, acetonitirle and mixtures thereof. The aprotic solvent is preferably tetrahydrofuran or acetonitirle, and more preferably acetonitirle.

In an embodiment, the amount of the aprotic solvent used ranges from 1 to 30 ml, and preferably from 10 to 28 ml, relative to one gram of the compound of the formula (II) used in step (i).

In an embodiment, the reaction temperature in step (iii) ranges from room temperature to reflux temperature.

In an embodiment, the reaction pressure in step (iii) ranges from normal pressure to 20 atm.

In an embodiment, the compound of the formula (III) is used in step (iii) in such an amount that a molar ratio of the compound of the formula (II) used in step (i) to the compound of the formula (III) ranges from 1:0.8 to 1:1.2, and preferably from 1:1 to 1:1.2.

The compound of the formula (I) prepared by the above-described process may be isolated and purified through experimental methods commonly used in organic chemistry field, for example, column chromatography, rectification, recrystallization and the like.

The compounds of the formula (II) are known, or can be prepared according to a method known per se (see, for example, A. C. Cope, Org. React. 1957, 9, 107). For example, a cyanoacetate compound reacts with a sodium alkoxide, and then with bromoisopropane via nucleophilic reaction, to form a 3-methyl-2-cyanobutyrate compound.

The compounds of the formula (III) are known, or can be prepared according to a method known per se (see, for example, Journal of the American Chemical Society, 1954, 76, 1137-1140). For example, ethyl 2-bromoisopentanoate is commercially available.

By the above-described process, for example, dimethyl 2,3-diisopropyl-2-cyanosuccinate, diethyl 2,3-diisopropyl-2-cyanosuccinate, 2,3-diisopropyl-2-cyanosuccinic acid 1-methyl ester-4-ethyl ester ($R^1$=methyl, $R^2$=ethyl), and 2,3-diisopropyl-2-cyanosuccinic acid 1-ethyl ester-4-methyl ester ($R^1$=ethyl, $R^2$=methyl) can be obtained.

Figure 1:
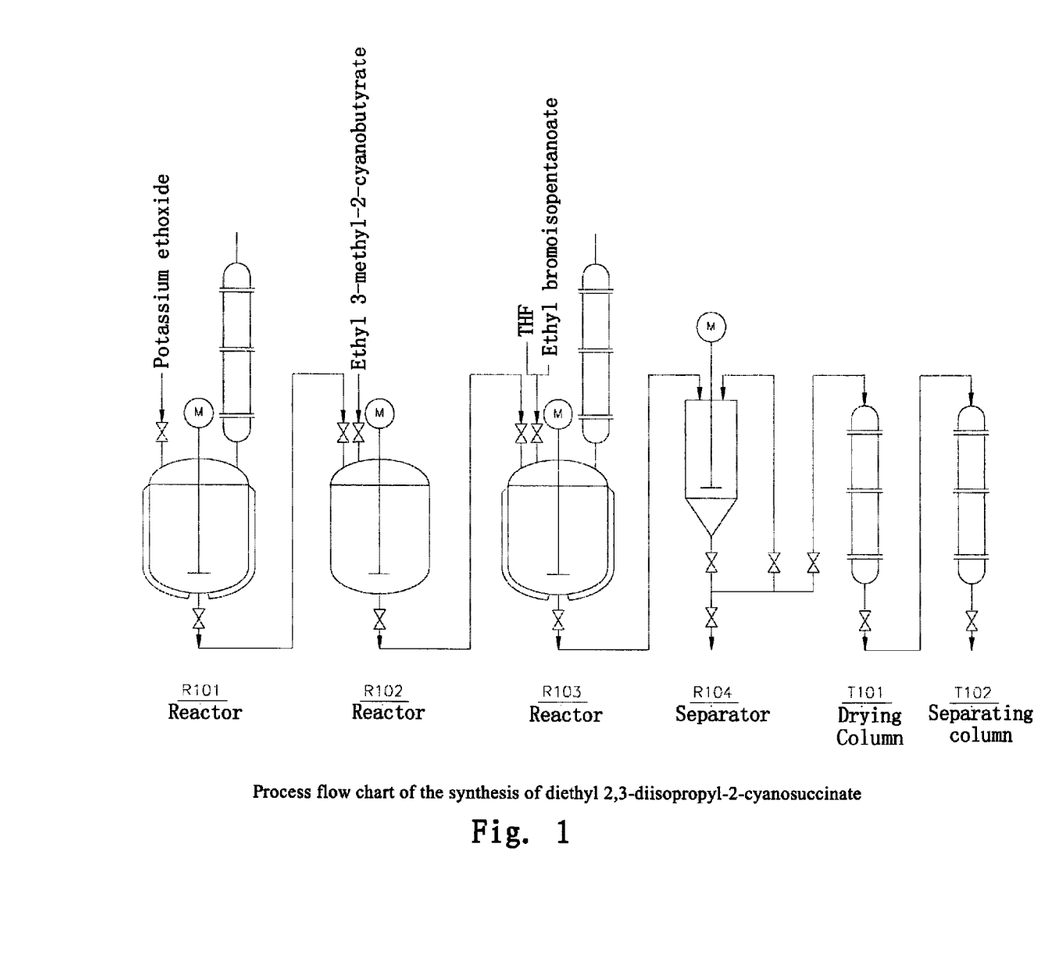
FIG. 1 is a process flow chart of the preparation of a diester of a 2,3-diisopropyl-2-cyanosuccinic acid according to an embodiment of the invention.

With reference to FIG. 1, a preferred embodiment of the invention will be described below, wherein diethyl 2,3-diisopropyl-2-cyanosuccinate is prepared. Absolute ethanol and metallic potassium are charged into a reactor R101, or potassium ethoxide and absolute ethanol are charged into the reactor R101, to prepare a solution of potassium ethoxide; ethyl 3-methyl-2-cyanobutyrate is charged into a reactor R102, and then the prepared solution of potassium ethoxide is added thereto at a temperature ranging from −10° C. to 45° C.; upon the completion of the reaction, the reaction mixture is transferred to a reactor R103 and the solvent is removed, then tetrahydrofuran or acetonitirle is added thereto, followed by the addition of ethyl 2-bromoisopentanoate, and then the reaction mixture is heated to reflux; upon the completion of the reaction, the solvent is removed again, the resultant mixture is transferred to a separator R104, water is added thereto to dissolve solids, and the mixture is extracted with diethyl ether or methyl tert-butyl ether; the extract liquor is passed through a drying column T101 so as to be dried, and then is fed to a separating column T102, where diethyl 2,3-diisopropyl-2-cyanosuccinate is separated.

In a second aspect, the present invention provides a process for the preparation of a 2,3-di(non-linear-alkyl)succinic acid, comprising the steps of:

(i) obtaining a 2,3-di(non-linear-alkyl)-2-cyanosuccinate compound of the formula (I) by the above-described process according to the invention wherein, R, R¹ and R² are as defined above; and (ii) conducting hydrolysis and decarboxylation reaction of the 2,3-di(non-linear-alkyl)-2-cyanosuccinate compound in the presence of 60% to 90% sulfuric acid at a bath temperature of from 90° C. to 180° C., to form a 2,3-di(non-linear-alkyl)succinic acid.

In a preferred embodiment, the above hydrolysis and decarboxylation reaction in step (ii) is conducted in the presence of 62% to 70% sulfuric acid.

In a preferred embodiment, the above hydrolysis and decarboxylation reaction in step (ii) is conducted at a bath temperature of from 150° C. to 170° C.

Figure 2:
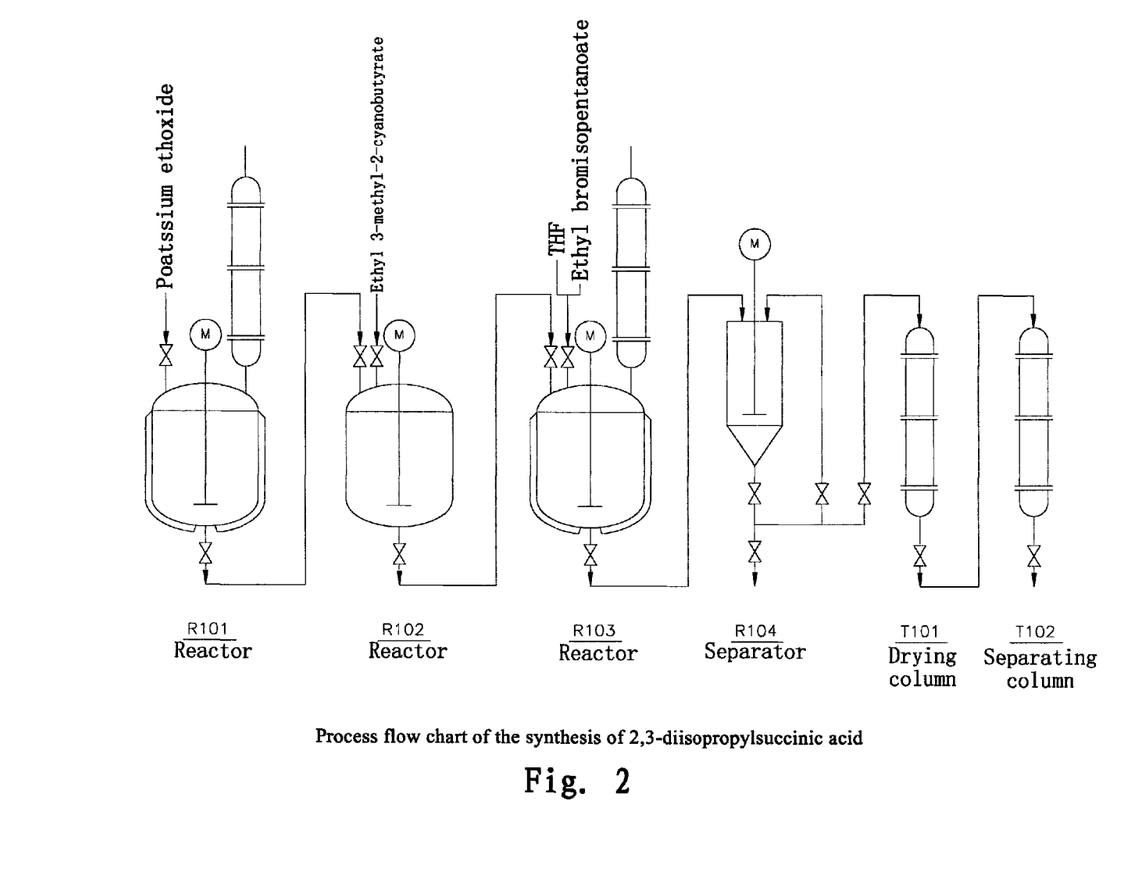
FIG. 2 is a process flow chart of the preparation of a 2,3-diisopropylsuccinic acid according to an embodiment of the invention.

In an embodiment, the present invention provides a process for the preparation of 2,3-diisopropylsuccinic acid. The synthesis scheme is shown below:

With reference to FIG. 2, a preferred embodiment of the invention will be described below, wherein 2,3-diisopropylsuccinic acid is obtained. Absolute ethanol and metallic potassium are charged into a reactor R101, or potassium ethoxide and absolute ethanol are charged into the reactor R101, to prepare a solution of potassium ethoxide; ethyl 3-methyl-2-cyanobutyrate is charged into a reactor R102, and then the prepared solution of potassium ethoxide is added thereto at a temperature ranging from −10° C. to 45° C.; upon the completion of the reaction, the reaction mixture is transferred to a reactor R103 and the solvent is removed, then tetrahydrofuran or acetonitrile is added thereto, followed by the addition of ethyl 2-bromoisopentanoate, and then the reaction mixture is heated to reflux; upon the completion of the reaction, the solvent is removed again, the resultant mixture is transferred to a separator R104, water is added thereto to dissolve solids, and the mixture is extracted with diethyl ether or methyl tert-butyl ether; the extract liquor is passed through a drying column T101 so as to be dried, and then is fed to a separating column T102, where diethyl 2,3-diisopropyl-2-cyanosuccinate is separated; the diethyl 2,3-diisopropyl-2-cyanosuccinate is added into a reactor R201, and a 60-90% aqueous solution of sulfuric acid is added dropwise thereto to conduct hydrolysis and decarboxylation reaction; upon the completion of the reaction, the reaction mixture is diluted with water and transferred to a separator R202 to be extracted with methyl tert-butyl ether; the obtained methyl tert-butyl ether extract liquor is charged into a reactor R203, and an aqueous solution of potassium hydroxide is added thereto; then the reaction mixture is transferred to a separator R204 to be separated; an aqueous layer separated is acidized with hydrochloric acid in a reactor R205 to obtain precipitates; the precipitates are centrifugally dried in a centrifuge C201, and then dried to afford 2,3-diisopropylsuccinic acid.

In a third aspect, the present invention provides a process for the preparation of a 2,3-di(non-linear-alkyl)succinate, comprising the steps of:

(i) obtaining a 2,3-di(non-linear-alkyl)-2-cyanosuccinate compound by the above process according to the present invention;

(ii) conducting hydrolysis reaction and decarboxylation reaction in the presence of a 60% to 90% sulfuric acid at a bath temperature of from 90° C. to 180° C., to form a 2,3-di(non-linear-alkyl)succinic acid; and (iii) reacting the 2,3-di(non-linear-alkyl)succinic acid with an alcohol under an acidic condition, to obtain a 2,3-di(non-linear-alkyl)succinate, wherein the alcohol is selected from the group consisting of methanol, ethanol, propanol, isopropanol, butanol, iso-butanol and mixtures thereof; or reacting the 2,3-di(non-linear-alkyl)succinic acid with a haloalkane or a diester of sulfuric acid under a basic condition, to form a 2,3-di(non-linear-alkyl)succinate, wherein the haloalkane is selected from the group consisting of halomethane, haloethane, halopropane, haloisopropane, halobutane, haloisobutane and mixtures thereof, and the diester of sulfuric acid is selected from the group consisting of dimethyl sulfate, diethyl sulfate, dibutyl sulfate and mixtures thereof.

Methods for esterifying the 2,3-di(non-linear-alkyl)succinic acids are known per se. See, for example, CN1313869A and Vogel's Textbook of Practical Organic Chemistry, 5th Ed, 1989, 695-706. Preferably, the 2,3-di(non-linear-alkyl)succinates are obtained by reacting the 2,3-di(non-linear-alkyl)succinic acids with an alcohol in the presence of concentrated sulfuric acid.

By the above process according to the present invention, for example, dimethyl 2,3-diisopropylsuccinate, diethyl 2,3-diisopropylsuccinate, di-n-propyl 2,3-diisopropylsuccinate, di-n-butyl 2,3-diisopropylsuccinate, di-iso-butyl 2,3-diisopropylsuccinate, di-iso-pentyl 2,3-diisopropylsuccinate, di-iso-hexyl 2,3-diisopropylsuccinate, di-2-methylhexyl 2,3-diisopropylsuccinate can be obtained.

Figure 3:
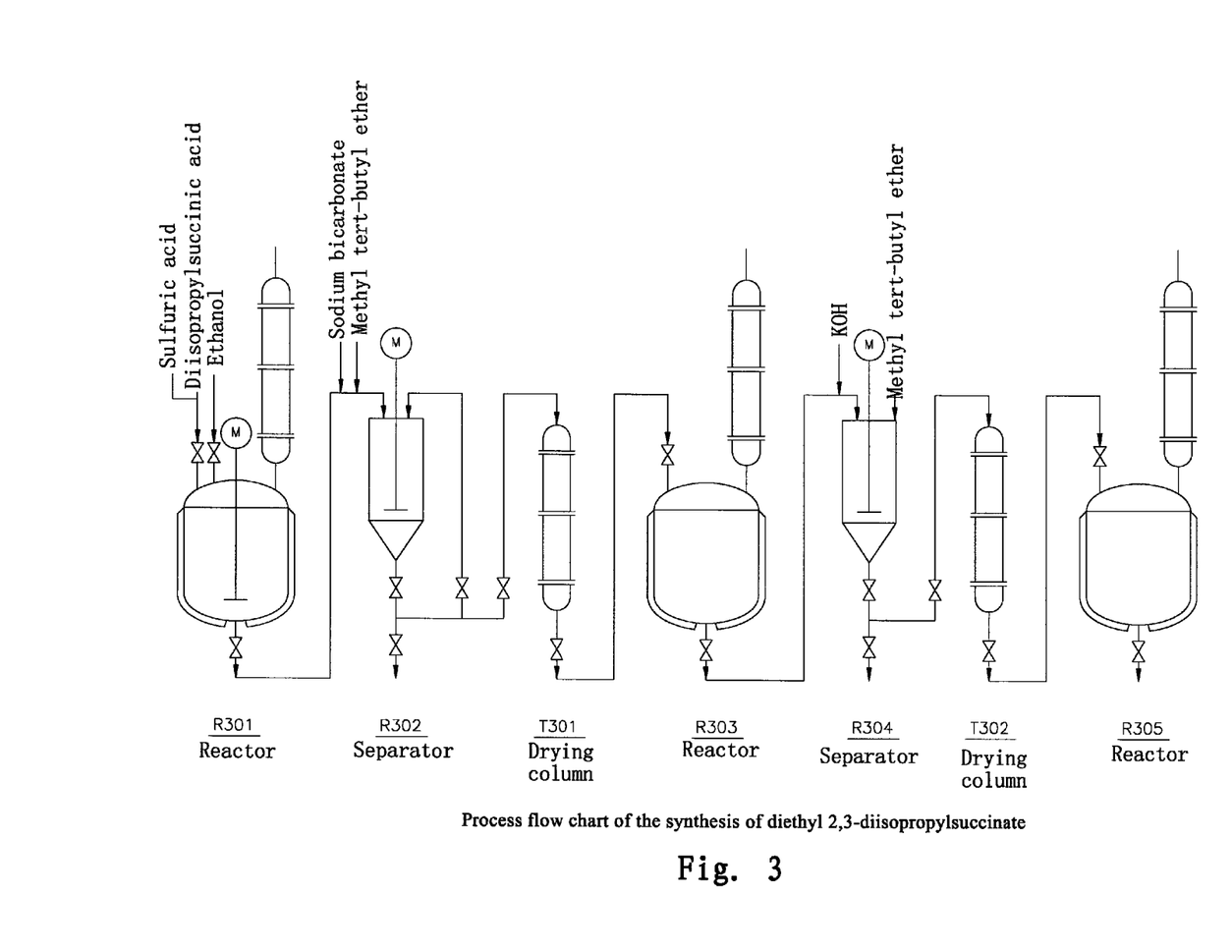
FIG. 3 is a process flow chart of the preparation of a diethyl 2,3-diisopropylsuccinate according to an embodiment of the invention.

With reference to FIG. 3, a preferred embodiment of the invention will be described below, wherein diethyl 2,3-diisopropylsuccinate is obtained. Absolute ethanol and metallic potassium are charged into a reactor R101, or potassium ethoxide and absolute ethanol are charged into the reactor R101, to prepare a solution of potassium ethoxide; ethyl 3-methyl-2-cyanobutyrate is charged into a reactor R102, and then the prepared solution of potassium ethoxide is added thereto at a temperature ranging from −10° C. to 45° C.; upon the completion of the reaction, the reaction mixture is transferred to a reactor R103 and the solvent is removed, then tetrahydrofuran or acetonitirle is added thereto, followed by the addition of ethyl 2-bromoisopentanoate, and then the reaction mixture is heated to reflux; upon the completion of the reaction, the solvent is removed again, the resultant mixture is transferred to a separator R104, water is added thereto to dissolve solids, and the mixture is extracted with diethyl ether or methyl tert-butyl ether; the extract liquor is passed through a drying column T101 so as to be dried, and then is fed to a separating column T102, where diethyl 2,3-diisopropyl-2-cyanosuccinate is separated; the diethyl 2,3-diisopropyl-2-cyanosuccinate is added into a reactor R201, and a 60-90% aqueous solution of sulfuric acid is added dropwish thereto to conduct hydrolysis and decarboxylation reaction; upon the completion of the reaction, the reaction mixture is diluted with water and transferred to a separator R202 to be extracted with methyl tert-butyl ether; the obtained methyl tert-butyl ether extract liquor is charged into a reactor R203, and an aqueous solution of potassium hydroxide is added thereto; then the reaction mixture is transferred to a separator R204 to be separated; an aqueous layer separated is acidized with hydrochloric acid in a reactor R205 to obtain precipitates; the precipitates are centrifugally dried in a centrifuge C201, and then dried to afford 2,3-diisopropylsuccinic acid; the 2,3-diisopropylsuccinic acid and absolute ethanol are charged into a reactor R301, and a catalytic amount of sulfuric acid is added thereto, to conduct esterification reaction; upon the completion of the reaction, the ethanol is removed, and methyl tert-butyl ether is added into the reaction mixture; the resultant mixture is transferred to a separator R302 and wished with an aqueous solution of sodium bicarbonate; the organic layer is passed through a drying column T301 so as to be dried, and then is fed to a reactor R303, where the solvent is removed to obtain a crude product; the obtained crude product is fed to a separator R304, wished there with an aqueous solution of potassium hydroxide, and extracted with methyl tert-butyl ether; the extract liquor is dried in a drying column T302, and then fed to a reactor R305, where the solvent is removed to obtain diethyl 2,3-diisopropylsuccinate.

EXAMPLES

The following examples are given for further illustrating the invention, but do not make limitation to the invention in any way.

Example 1

Preparation of diethyl 2,3-diisopropyl-2-cyanosuccinate

Under nitrogen atmosphere, 0.37 g of metallic potassium was added into 40 ml of absolute ethanol, to prepare potassium ethoxide. The prepared potassium ethoxide was added dropwise into a 100 ml flask containing 1.48 g of ethyl 3-methyl-2-cyanobutyrate. The reaction mixture was stirred at room temperature for 1 h, and then evaporated off the solvent to afford white solids. The white solids were dissolved in 25 ml of tetrahydrofuran, and then the resultant solution was slowly added dropwise into a solution of 2.2 g of ethyl 2-bromoisopentanoate in 30 ml of tetrahydrofuran, and the reaction mixture was heated to reflux for 9 h. Then the solvent was evaporated, to afford a mixture of yellow sticky liquid and pale yellow solids. To this mixture were added with 75 ml of diethyl ether and 20 ml of water, and an organic phase was separated. The organic phase was washed with 20 ml of 10% aqueous $NaHCO_3$ solution twice, and then with water until the organic phase was neutral. The organic phase was dried over anhydrous magnesium sulfate over night, filtered, and evaporated off the solvent, to afford a yellow clear liquid. The yellow clear liquid was separated on a silica chromatographic column (eluent: petroleum ether and chloroform), to afford a pale yellow clear liquid.

High resolution Electrospray ionization (ESI) mass spectrometry: 284.1897, 306.1656, which are consistent with the mass of M+H (calculated value: 284.1863) and M+Na (calculated value: 306.1681) of compound $C_{15}H_{25}NO_4$, respectively.

Low resolution mass spectrometer analysis (EI, m/z): 283 $(M^+)$, 284 (M+1), 268 $(M-15)^+$, 241 $(M-42)^+$, 238 $(M-45)^+$, 210, 198, 168, 140, 129, 122, 115.

IR $(cm^{-1})$: 2979, 2881, 2246, 1733, 1469, 1394, 1371, 1299.6, 1141.

$^1H$ NMR ($CDCl_3$/TMS, 300 MHZ) (δ ppm): 0.999-1.148 (2d, 6H, $CH(CH_3)_2$), 1.213-1.378 (m, 12H: $CH(CH_3)_2$; J=7.2 Hz, $2CH_2CH_3$), 2.096-2.148 (m, 1H, $CHCH(CH_3)_2$), 2.304-2.372 (m, 1H, $CH(CH_3)_2$), 3.012 & 3.019 (d, 1H, O=$CCHCH(CH_3)_2$), 4.144-4.284 (2q, J=7.2 Hz, 4H, $2OCH_2$).

Example 2

Preparation of diethyl 2,3-diisopropyl-2-cyanosuccinate

The procedure described in Example 1 was repeated, except that acetonitrile was used in place of the tetrahydrofuran solvent, to obtain diethyl 2,3-diisopropyl-2-cyanosuccinate (yield: 64%). The mass spectrum and IR spectrum of the product are consistent with the structure of the target compound.

Example 3

Preparation of 2,3-diisopropyl succinic acid 10 ml of 95% concentrated sulfuric acid was slowly added dropwise into 5 ml of water, and the mixture was cooled to room temperature, to obtain a sulfuric acid solution. The prepared sulfuric acid solution was added into a three-necked flask containing 0.22 g of diethyl 2,3-diisopropyl-2-cyanosuccinate, and the reaction mixture was stirred at an oil-bath temperature of 160° C. for 16 h. Upon the completion of the reaction, the reaction mixture was cooled to room temperature, diluted with 30 ml of water, and cooled to room temperature again. The reaction mixture was extracted with anhydrous diethyl ether, and the solvent was removed from the extract liquor, to afford a mixture of white solids and oily liquid. This mixture was dissolved in 10 ml of 10% aqueous KOH solution, and the resultant solution was stirred at 50° C. for 45 min. The reaction mixture was extracted with diethyl ether, and the organic phase was discarded. The aqueous phase was acidified with concentrated hydrochloric acid, whereby white precipitates formed. The precipitates were filtered and dried, to afford the product, 2,3-diisopropyl succinic acid (yield: 60%).

Low resolution mass spectrometer analysis (EI, m/z): 185 $(M-17)^+$, 160 $(M-42)^+$.

IR (cm$^{-1}$): 2968, 2940, 2884, 2698, 1703, 1468, 1439, 1392, 1377, 1278, 1247, 1217, 1179, 1133, 946, 756.

Example 4

Preparation of diethyl 2,3-diisopropyl succinate

In a 100 ml single-necked flask, 1 g of 2,3-diisopropylsuccinic acid was dissolved in 60 ml of absolute ethanol. 0.5 ml of concentrated sulfuric acid was added dropwise to the flask. The reaction mixture was stirred at reflux temperature for 24 h. Then the reaction mixture was cooled to room temperature and evaporated off ethanol, thereby affording a pale yellow viscous liquid. The viscous liquid was dissolved in anhydrous diethyl ether and washed with 10% aqueous NaHCO$_3$ solution. The organic phase was washed with water to neutrality and dried over anhydrous magnesium sulfate over night. The magnesium sulfate was filtered off and the diethyl ether was removed, to afford 0.88 g crude product. The crude product was combined with 10% aqueous KOH solution, and then the mixture of the crude product and the aqueous KOH solution was extracted with diethyl ether, and the organic phase was dried over magnesium sulfate over night. The magnesium sulfate was filtered off and the solvent was removed, to afford purified target compound, diethyl 2,3-diisopropylsuccinate.

Low resolution mass spectrometer analysis (EI, m/z): 216 (M–42)$^+$, 213 (M–45)$^+$.

IR (cm$^{-1}$): 2965, 2934, 2876, 1732, 1465, 13912, 1374, 1264, 1227, 1241, 1179, 1159, 1116, 1030, 926.

Example 5

Preparation of diethyl 2,3-diisopropyl-2-cyanosuccinate

The procedure described in Example 1 was repeated, except that 0.22 g of metallic sodium was used in place of 0.37 g of metallic potassium, to obtain diethyl 2,3-diisopropyl-2-cyanosuccinate (yield: 59%). The mass spectrum and IR spectrum of the product are consistent with the structure of the target compound.

Example 6

Preparation of 2,3-diisopropylsuccinic acid

The procedure described in Example 3 was repeated, except that in the two product extraction separation operations, methyl tert-butyl ether was used to replace for the anhydrous diethyl ether and diethyl ether, respectively, to extract organics, thereby obtaining 2,3-diisopropylsuccinic acid (yield: 71%). The mass spectrum and IR spectrum of the product are consistent with the structure of the target compound.

The patents, patent applications and testing methods cited in the specification are incorporated herein by reference.

While the invention has been described with reference to exemplary embodiments, it will be understood by those skilled in the art that various changes and modifications may be made without departing from the spirit and scope of the invention. Therefore, the invention is not limited to the particular embodiments disclosed as the best mode contemplated for carrying out this invention, but the invention will include all embodiments falling within the scope of the appended claims.

What is claimed is:

1. A process for preparation of a compound of formula (I), comprising:
(i) reacting a compound of formula (II)

with at least one metal alkoxide in at least one alcohol solvent;
(ii) removing the alcohol solvent to obtain a concentrate;
(iii) dissolving the concentrate obtained in (ii) in at least one aprotic solvent, and then reacting it with a compound of formula (III), wherein,
$R^1$ and $R^2$ are independently selected from linear and branched $C_1$ to $C_{20}$ alkyl, $C_3$ to $C_{20}$ cycloalkyl, $C_4$ to $C_{20}$ alkylcycloalkyl, $C_4$ to $C_{20}$ cycloalkylalkyl, $C_6$ to $C_{20}$ aryl, $C_7$ to $C_{20}$ alkaryl and $C_7$ to $C_{20}$ aralkyl; and R is independently selected from $C_3$ to $C_6$ isoalkyl, $C_3$ to $C_6$ sec-alkyl and $C_3$ to $C_6$ cycloalkyl.

2. The process of claim 1, wherein:
the at least one metal alkoxide used in step (i) is selected from potassium methoxide, potassium ethoxide, potassium propoxide, potassium isopropoxide, potassium butoxide, potassium iso-butoxide, potassium tert-butoxide, sodium methoxide, sodium ethoxide, sodium propoxide, sodium isopropoxide, sodium butoxide, sodium iso-butoxide, and sodium tert-butoxide;
the molar ratio of the compound of formula (II) to the at least one metal alkoxide ranges from 1:0.8 to 1:1.2;
the at least one alcohol solvent used in step (i) is selected from methanol, ethanol, propanol, isopropanol, butanol, iso-butanol, and tert-butanol;
the amount of the at least one alcohol solvent used in step (i) ranges from 1 to 50 ml of the at least one alcohol per gram of the compound of formula (II);
the reaction temperature in step (I) ranges from –10° C. to 45° C.;
the removing of the alcohol solvent in step (ii) is carried out via atmospheric distillation or vacuum distillation;
the at least one aprotic solvent used in step (iii) is selected from tetrahydrofuran, dimethyl formamide, dimethyl sulfoxide, and acetonitrile;
the amount of the at least one aprotic solvent used in step (iii) ranges from 1 to 30 ml per gram of the compound of formula (II) used in step (i);
the reaction temperature in step (iii) ranges from room temperature to reflux temperature;
the reaction pressure in step (iii) ranges from normal pressure to 20 atm; or the amount of the compound of formula (III) used in step (iii) ranges from 0.8 to 1.2 moles per mole of the compound of formula (II) used in step (i).

3. The process of claim 2, wherein:
the at least one metal alkoxide used in step (i) is selected from potassium methoxide, potassium ethoxide, and potassium tert-butoxide;
the molar ratio of the compound of formula (II) to the at least one metal alkoxide ranges from 1:1 to 1:1.2;
the at least one alcohol solvent used in step (i) is selected from methanol, ethanol, and tert-butanol;
the amount of the at least one alcohol solvent used in step (i) ranges from 10 to 40 ml per gram of the compound of formula (II);
the reaction temperature in step (i) ranges from −5° C. to 40° C.; or
the at least one aprotic solvent used in step (iii) is selected from tetrahydrofuran and acetonitrile.

4. The process of claim 2, wherein:
the at least one metal alkoxide used in step (i) is potassium ethoxide;
the at least one alcohol solvent used in step (i) is ethanol;
the amount of the at least one alcohol solvent used in step (i) ranges from 15 to 25 ml per gram of the compound of formula (II);
the molar ratio of the compound of formula (II) to the at least one metal alkoxide is 1:1;
the reaction temperature in step (i) is room temperature;
the at least one aprotic solvent used in step (iii) is acetonitrile;
the reaction temperature in step (iii) is reflux temperature;
the reaction pressure in step (iii) is normal pressure; or
the amount of the compound of formula (III) used in step (iii) ranges from 1 to 1.2 moles per mole of the compound of formula (II) used in step (i).

5. The process of claim 1, wherein $R^1$ and $R^2$ are independently selected from $C_1$ to $C_8$ alkyl.

6. The process of claim 1, wherein $R^1$ and $R^2$ are independently selected from methyl, ethyl, propyl, butyl and isobutyl.

7. The process of claim 1, wherein both $R^1$ and $R^2$ are ethyl.

8. The process of claim 1, wherein R is independently isopropyl or iso-butyl.

9. The process of claim 1, wherein the compound of formula (I) is selected from compounds of formula (IV)

the compound of formula (II) is selected from compounds of formula (V)

the at least one metal alkoxide used in step (i) is at least one potassium alkoxide; and the compound of formula (III) is selected from compounds of formula (VI);

wherein $R^1$ and $R^2$ are independently selected from linear and branched $C_1$ to $C_{20}$ alkyl, $C_3$ to $C_{20}$ cycloalkyl, $C_4$ to $C_{20}$ alkylcycloalkyl, $C_4$ to $C_{20}$ cycloalkylalkyl, $C_6$ to $C_{20}$ aryl, $C_7$ to $C_{20}$ alkaryl, and $C_7$ to $C_{20}$ aralkyl.

10. The process of claim 9, wherein
the at least one potassium alkoxide used in step (i) is selected from potassium methoxide, potassium ethoxide, potassium propoxide, potassium isopropoxide, potassium butoxide, potassium iso-butoxide and potassium tert-butoxide;
the molar ratio of the compound of formula (V) to the at least one potassium alkoxide compound ranges from 1:0.8 to 1:1.2;
the at least one alcohol solvent used in step (i) is selected from methanol, ethanol, propanol, isopropanol, butanol, iso-butanol, and tert-butanol;
the amount of the at least one alcohol solvent used in step (i) ranges from 1 to 50 ml per gram of the compound of formula (V);
the reaction temperature in step (i) ranges from −10° C. to 45° C.;
the removing of the alcohol solvent in step (ii) is carried out via atmospheric distillation or vacuum distillation;
the at least one aprotic solvent used in step (iii) is selected from tetrahydrofuran, dimethyl formamide, dimethyl sulfoxide, and acetonitrile;
the amount of the at least one aprotic solvent used in step (iii) ranges from 1 to 30 ml per gram of the compound of formula (V) used in step (i);
the reaction temperature in step (iii) ranges from room temperature to reflux temperature;
the reaction pressure in step (iii) ranges from normal pressure to 20 atm; or
the amount of the compound of formula (VI) ranges from 0.8 to 1.2 moles per mole of the compound of formula (V) used in step (i).

11. The process of claim 10, wherein
the at least one potassium alkoxide used in step (i) is selected from potassium methoxide, potassium ethoxide, and potassium tert-butoxide;
the at least one alcohol solvent used in step (i) is selected from methanol, ethanol, and tert-butanol;
the amount of the at least one alcohol solvent used in step (i) ranges from 10 to 40 ml per gram of the compound of formula (V);
the reaction temperature in step (i) ranges from −5° C. to 40° C.; and
the at least one aprotic solvent used in step (iii) is selected from tetrahydrofuran, and acetonitrile.

12. The process of claim 1, wherein the compound of formula (I) is diethyl 2,3-diisopropyl-2-cyanosuccinate, comprising:
charging absolute ethanol and metallic potassium into a reactor (R101), or charging potassium ethoxide and absolute ethanol into a reactor (R101), to prepare a solution of potassium ethoxide;

charging ethyl 3-methyl-2-cyanobutyrate into a reactor (R102), and then adding the solution of potassium ethoxide at a temperature ranging from −10° C. to 45° C.;

transferring the reaction mixture from the reactor (R102) to a reactor (R103) and removing the solvent, then adding tetrahydrofuran or acetonitrile thereto, followed by the addition of ethyl 2-bromoisopentanoate, and then heating the reaction mixture to reflux;

removing the solvent, transferring the resultant mixture to a separator (R104), adding water thereto to dissolve solids, and extracting the mixture with diethyl ether or methyl tert-butyl ether;

passing the extract liquor through a drying column (T101), which is subsequently fed to a separating column (T102) to separate diethyl 2,3-diisopropyl-2-cyanosuccinate.

13. A process for preparation of a 2,3-di(non-linear-alkyl) succinic acid, wherein the non-linear-alkyl is independently selected from $C_3$ to $C_6$ isoalkyl, $C_3$ to $C_6$ sec-alkyl and $C_3$ and $C_6$ cycloalkyl, the process comprising:

reacting a compound of formula (I) with 60% to 90% sulfuric acid at a bath temperature ranging from 90° C. to 180° C., (I)

wherein the compound of formula (I) is prepared according to a method comprising:
(i) reacting a compound of formula (II)

(II)

with at least one metal alkoxide in at least one alcohol solvent;
(ii) removing the alcohol solvent to obtain a concentrate;
(iii) dissolving the concentrate obtained in (ii) in at least one aprotic solvent, and then reacting it with a compound of formula (III), (III)

wherein,
$R^1$ and $R^2$ are independently selected from linear and branched $C_1$ to $C_{20}$ alkyl, $C_3$ to $C_{20}$ cycloalkyl, $C_4$ to $C_{20}$ alkylcycloalkyl, $C_4$ to $C_{20}$ cycloalkylalkyl, $C_6$ to $C_{20}$ aryl, $C_7$ to $C_{20}$ alkaryl and $C_7$ to $C_{20}$ aralkyl; and R is independently selected from $C_3$ to $C_6$ isoalkyl, $C_3$ to $C_6$ sec-alkyl and $C_3$ to $C_6$ cycloalkyl.

14. The process of claim 13, wherein the di-carboxylic acid is 2,3-diisopropylsuccinic acid, comprising:

charging absolute ethanol and metallic potassium into a reactor (R101), or charging potassium ethoxide and absolute ethanol into a reactor (R101), to prepare a solution of potassium ethoxide;

charging ethyl 3-methyl-2-cyanobutyrate into a reactor (R102), and then adding the solution of potassium ethoxide thereto at a temperature ranging from −10° C. to 45° C.;

transferring the reaction mixture from the reactor (R102) to a reactor (R103) and removing the solvent, then adding tetrahydrofuran or acetonitrile thereto, followed by the addition of ethyl 2-bromoisopentanoate, and then heating the reaction mixture to reflux;

removing the solvent, transferring the resultant mixture to a separator (R104), adding water thereto to dissolve solids, and extracting the mixture with diethyl ether or methyl tert-butyl ether;

passing the extract liquor through a drying column (T101), which is subsequently fed to a separating column (T102) to separate diethyl 2,3-diisopropyl-2-cyanosuccinate;

charging the diethyl 2,3-diisopropyl-2-cyanosuccinate into a reactor (R201), and subsequently adding a 60-90% aqueous solution of sulfuric acid drop-wise thereto;

diluting the reaction mixture with water, and transferring the resulting mixture to a separator (R202), which is subsequently extracted with methyl tert-butyl ether;

charging the obtained methyl tert-butyl ether extract liquor into a reactor (R203), and adding an aqueous solution of potassium hydroxide thereto;

transferring the reaction mixture from the reactor (R203) to a separator (R204);

acidifying an aqueous layer separated with hydrochloric acid in a reactor (R205) to obtain precipitates;

centrifugally drying the precipitates in a centrifuge (C201), which is then dried to afford 2,3-diisopropylsuccinic acid.

15. A process for preparation of a 2,3-di(non-linear-alkyl) succinate, wherein the non-linear-alkyl is independently selected from $C_3$ to $C_6$ isoalkyl, $C_3$ to $C_6$ sec-alkyl and $C_3$ to $C_6$ cycloalkyl, and wherein the alkyl moiety of the succinate is selected from methyl, ethyl, propyl, isopropyl, butyl, and isobutyl, the process comprising:

reacting a compound of formula (I) with 60% to 90% sulfuric acid at a bath temperature ranging from 90° C. to 180° C., to form a di-carboxylic acid; and (I)

reacting the di-carboxylic acid with at least one alcohol under an acidic condition, wherein the at least one alcohol is selected from methanol, ethanol, propanol, iso-propanol, butanol, and iso-butanol; or reacting the di-carboxylic acid with at least one haloalkane or at least one diester of sulfuric acid under a basic condition, wherein the at least one haloalkane is selected from halomethane, haloethane, halopropane, haloisopropane, halobutane, and haloisobutane, and the at least one diester of sulfuric acid is selected from dimethyl sulfate, diethyl sulfate, and dibutyl sulfate, and further wherein the compound of formula (I) is prepared according to a method comprising:

(i) reacting a compound of formula (II)

(II)

with at least one metal alkoxide in at least one alcohol solvent;

(ii) removing the alcohol solvent to obtain a concentrate;

(iii) dissolving the concentrate obtained in (ii) in at least one aprotic solvent, and then reacting it with a compound of formula (III), (III)

wherein, $R^1$ and $R^2$ are independently selected from linear and branched $C_1$ to $C_{20}$ alkyl, $C_3$ to $C_{20}$ cycloalkyl, $C_4$ to $C_{20}$ alkylcycloalkyl, $C_4$ to $C_{20}$ cycloalkylalkyl, $C_6$ to $C_{20}$ aryl, $C_7$ to $C_{20}$ alkaryl and $C_7$ to $C_{20}$ aralkyl; and R is independently selected from $C_3$ to $C_6$ isoalkyl, $C_3$ to $C_6$ sec-alkyl and $C_3$ to $C_6$ cycloalkyl.

16. The process of claim 15, wherein the di-carboxylate is diethyl 2,3-diisopropylsuccinate, comprising:

(1)—charging absolute ethanol and metallic potassium into a reactor (R101), or charging potassium ethoxide and absolute ethanol into a reactor (R101), to prepare a solution of potassium ethoxide;

charging ethyl 3-methyl-2-cyanobutyrate into a reactor (R102), and then adding the solution of potassium ethoxide thereto at a temperature ranging from −10° C. to 45° C.;

transferring the reaction mixture from the reactor (R102) to a reactor (R103) and removing the solvent, then adding tetrahydrofuran or acetonitrile thereto, followed by the addition of ethyl 2-bromoisopentanoate, and then heating the reaction mixture to reflux;

removing the solvent, transferring the resultant mixture to a separator (R104), adding water thereto to dissolve solids, and extracting the mixture with diethyl ether or methyl tert-butyl ether;

passing the extract liquor through a drying column (T101), which is subsequently fed to a separating column (T102) to separate diethyl 2,3-diisopropyl-2-cyanosuccinate;

(2)—charging the diethyl 2,3-diisopropyl-2-cyanosuccinate into a reactor (R201), and subsequently adding a 60-90% aqueous solution of sulfuric acid drop-wise thereto;

diluting the reaction mixture with water, and transferring the resulting mixture to a separator (R202), which is subsequently extracted with methyl tert-butyl ether;

charging the obtained methyl tert-butyl ether extract liquor into a reactor (R203), and adding an aqueous solution of potassium hydroxide thereto;

transferring the reaction mixture from the reactor (R203) to a separator (R204);

acidifying an aqueous layer separated with hydrochloric acid in a reactor (R205) to obtain precipitates;

centrifugally drying the precipitates in a centrifuge (C201), which is then dried to afford 2,3-diisopropylsuccinic acid;

(3)—charging the 2,3-diisopropylsuccinic acid and absolute ethanol into a reactor (R301), and adding a catalytic amount of sulfuric acid thereto;

removing the ethanol, and adding methyl tert-butyl ether thereto;

transferring the resultant mixture to a separator (R302) and washing the resultant mixture with an aqueous solution of sodium bicarbonate;

passing the organic layer through a drying column (T301), which then is fed to a reactor (R303), where the solvent is removed to obtain a crude product;

feeding the obtained crude product to a separator (R304), which is subsequently washed with an aqueous solution of potassium hydroxide, and extracted with methyl tert-butyl ether;

passing the methyl tert-butyl ether extract liquor in a drying column (T302), which is then fed to a reactor (R305) to remove the solvent.

* * * * *